United States Patent
Ono et al.

(10) Patent No.: US 8,362,468 B2
(45) Date of Patent: Jan. 29, 2013

(54) MICRO-CHANNEL CHIP AND MICRO-ANALYSIS SYSTEM

(75) Inventors: Koichi Ono, Saitama (JP); Tomoki Nakao, Saitama (JP); Akira Niwayama, Saitama (JP)

(73) Assignee: Enplas Corporation, Saitama (JP)

( * ) Notice: Subject to any disclaimer, the term of this patent is extended or adjusted under 35 U.S.C. 154(b) by 197 days.

(21) Appl. No.: 12/845,900

(22) Filed: Jul. 29, 2010

(65) Prior Publication Data

US 2011/0241134 A1  Oct. 6, 2011

(30) Foreign Application Priority Data

Mar. 31, 2010  (JP) ................. 2010-083304

(51) Int. Cl.
- *H01L 29/08* (2006.01)
- *H01L 51/00* (2006.01)
- *H01L 27/14* (2006.01)

(52) U.S. Cl. .................. 257/40; 257/414; 257/E51.002

(58) Field of Classification Search .................. 257/40, 257/414, E51.002
See application file for complete search history.

(56) References Cited

U.S. PATENT DOCUMENTS

| | | | | |
|---|---|---|---|---|
| 8,147,774 | B2 * | 4/2012 | Hagiwara et al. | 422/502 |
| 2007/0122314 | A1 * | 5/2007 | Strand et al. | 422/100 |
| 2008/0057274 | A1 * | 3/2008 | Hagiwara et al. | 428/172 |
| 2008/0283875 | A1 * | 11/2008 | Mukasa et al. | 257/253 |
| 2009/0047695 | A1 * | 2/2009 | Wagner et al. | 435/15 |
| 2009/0278224 | A1 | 11/2009 | Kim et al. | |
| 2011/0257040 | A1 * | 10/2011 | Turner et al. | 506/16 |

OTHER PUBLICATIONS

Extended European Search Report for Appl. No. 11159774.6 dated Jul. 11, 2012.
Julien Bachmann et al, "A Practical, Self-Catalytic, Atomic Layer Deposition of Silicon Dioxide", Angewandte Chemie International Edition, vol. 47, No. 33, Aug. 4, 2008, pp. 6177-6179, XP55031049.
Jonathan G. Terry et al, "Improved Silicon Nitride Surfaces for Next-Generation Microarrays", Langmuir, vol. 22, No. 26, Dec. 1, 2006, pp. 11400-11404, XP55031054.

* cited by examiner

*Primary Examiner* — Ngan Ngo
(74) *Attorney, Agent, or Firm* — Kubotera & Associates, LLC

(57) ABSTRACT

A micro-channel chip can be coated uniformly with a thin inorganic oxide film and can prevent an ionic hydrophobic substance from adsorbing through a surface of an inorganic oxide film. In the micro-channel chip, surfaces of inner walls of through-holes in an upper plate member and a channel of a lower plate member are entirely coated with a $SiO_2$ film. The $SiO_2$ film is formed of two layers, namely a bottom layer that contains a high content of carbon atoms and is formed in a part that contacts a resin substrate, and a surface layer that contains nearly zero content of carbon atoms and t is formed in a part that is exposed on the surface of a channel.

5 Claims, 4 Drawing Sheets

(CHANNEL)

(CHANNEL)

MICRO-CHANNEL CHIP AND MICRO-ANALYSIS SYSTEM

CROSS REFERENCE TO RELATED APPLICATIONS

The disclosure of Japanese Patent Application No.2010-083304, filed on Mar. 31, 2010, including the specification, drawings and abstract, is incorporated herein by reference in its entirety.

TECHNICAL FIELD

The present invention relates to a micro-channel chip having a resin substrate, with a micro-channel formed inside, and a micro-analysis system including the micro-channel chip.

BACKGROUND ART

In recent years, in fields of science and medicine such as such as biochemistry and analytical chemistry, a micro-analysis system has been used in order to quickly and accurately examine and analyze a small amount of substance, such as protein and nucleic acid (for example, DNA).

A micro-analysis system forms micro-spaces that function as a channel having a width and depth of approximately several tens to two hundreds of micrometers, a reacting section, a separating section, an extracting section, a detecting section and so on, inside a micro-channel chip, injects a sample and a migration solution (buffer solution) into the channel, and carries out an analysis.

A glass substrate has been used for a micro-channel chip at first. However, since a glass substrate is expensive, in recent years, a micro-channel chip made of a resin that is mass-producible and inexpensive, has become popular.

However, with a micro-channel chip made of a resin, hydrophobic elements such as fluorescent dye and protein adsorb on the surface of a channel, which then produces various problems, including increased background occurrence of electro-osmotic flow. SDS (Sodium Dodecyl Sulphate), which is used for the electrophoresis of protein, also has a hydrophobic part. If this hydrophobic part adsorbs on the surface of a channel of a micro-channel chip made of a resin, electro-osmotic flow is produced, and, as a result, the accuracy of electrophoresis deteriorates.

Further, techniques for coating the surface of a channel of a micro-channel chip made of a resin with an inorganic oxide film such as a $SiO_2$ (silicon dioxide) film, to suppress electro-osmotic flow or prevent hydrophobic substance from adsorbing on the channel surface, have been disclosed. Meanwhile, coating with a $SiO_2$ film is advantageous in that it provides a stable material, imparts a hydrophilic property to the surface of a channel, and provides excellent transparency.

Patent Literature 1 discloses a technique of coating the channel part and bonding surface of a microchip substrates made of a resin with a $SiO_2$ film by a deposition method, a sputtering method, a chemical vapor deposition (CVD) method, or a coating method, and then bonding microchip substrates to each other by ultrasonic welding.

Patent Literature 2 discloses a technique of coating a channel with a $SiO_2$ film by dipping a microchip substrate made of plastic in a solvent supersaturated with $SiO_2$.

Patent Literature 3 discloses a technique of depositing silicon nitride and so on on the surface of a channel of a microchip substrate made of plastic, by a plasma CVD method.

Non-Patent Literature 1 describes a technique of coating a $SiO_2$ film by a catalyst CVD method.

Citation List
Patent Literature
Patent Literature 1: Japanese Patent Application Laid-Open No.2008-232885
Patent Literature 2: Japanese Patent Application Laid-Open No.2002-139419
Patent Literature 3: Japanese Patent Application Laid-Open No. 2006-153823
Non-Patent Literature
Non-Patent Literature 1: $SiO_2$ film growth at low temperatures by catalyzed atomic layer deposition in a viscous flow reactor (Thin Solid Films 491 (2005) 43-53)

SUMMARY OF INVENTION

Technical Problem

However, according to the technique disclosed in Patent Literature 1, the bonding surface is fused and bonded by ultrasonic welding after the bonding surface is coated. Accordingly, the cross-sectional shape of the channel is deformed, and consequently the accuracy of the dimensions is not guaranteed.

Further, according to the technique disclosed in Patent Literature 2, the $SiO_2$ film is formed several micrometers thick, and the cross-section area of a channel changes. Furthermore, according to the technique of Patent Literature 2, the use of a solvent results in significant management burden and increased cost.

Moreover, according to the plasma CVD method disclosed in Patent Literature 3, it is not possible to coat a surface which plasma does not hit.

Still further, according to the technique disclosed in Non-Patent Literature 1, since catalyst components (organic components such as pyridine) remain on the surface, ionic hydrophobic substance adsorbs on the catalyst parts.

It is therefore an object of the present invention to provide a micro-analysis system and a micro-channel chip by which the deformation of the cross-sectional shape of a channel is minimized, the interior of a channel is coated uniformly with a thin inorganic oxide film such as a $SiO_2$ film, and hydrophobic substance is prevented from adsorbing on the surface of an inorganic oxide film.

Solution of Problem

A micro-channel chip of the present invention employs a configuration having a resin substrate in which an inner wall surface of a channel is coated with an inorganic oxide film, and, in this micro-channel chip, the inorganic oxide film is formed with a plurality of layers, and the content of carbon or nitrogen atoms in the surface layer that exposes on the surface of the channel is lower than in the bottom layer which contacts the resin substrate.

A micro-analysis system of the present invention employs a configuration including the micro-channel chip.

ADVANTAGEOUS EFFECTS OF INVENTION

According to the present invention, a bottom layer containing a high content of carbon (C) or nitrogen (N) atoms is formed in a part that contacts a resin substrate, and a surface layer containing nearly zero content of carbon or nitrogen atoms is formed in a part that exposes on the surface of a channel. Accordingly, it is possible to coat a micro-channel chip uniformly with a thin inorganic oxide film, and prevent ionic hydrophobic substance from adsorbing on the surface of the inorganic oxide film.

DESCRIPTION OF EMBODIMENTS

An embodiment of the present invention will be described in detail below with reference to the drawings. Meanwhile, a case in which a $SiO_2$ film is formed as an inorganic oxide film will be described with the following embodiment.

[Structure of Micro-channel Chip]

Figure 1:
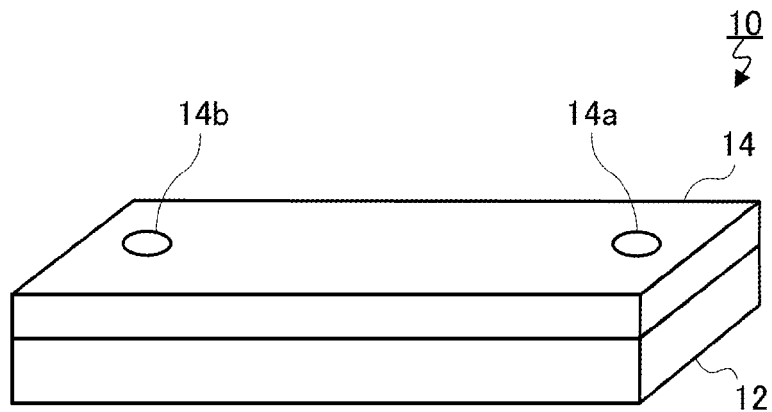
FIG. 1 is a perspective view showing a shape of a micro-channel chip according to an embodiment of the present invention.
Figure 2:
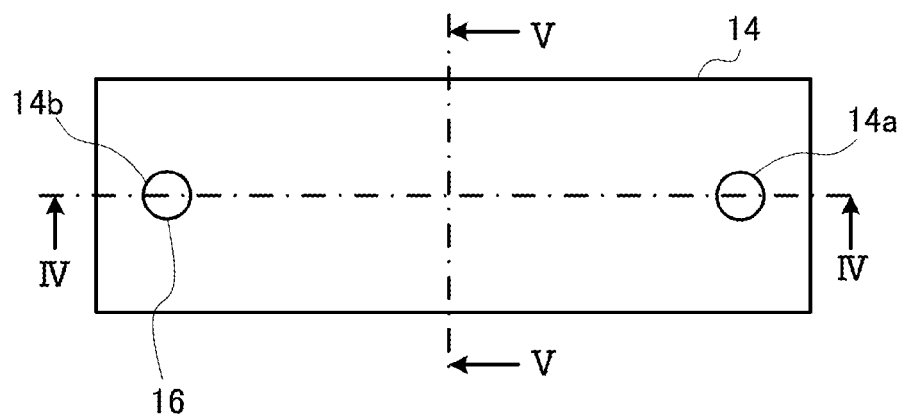
FIG. 2 is a plan view of the micro-channel chip shown in FIG. 1.

FIG. 1 is a perspective view showing the shape of a micro-channel chip according to an embodiment of the present invention. FIG. 2 is a plan view of the micro-channel chip of FIG. 1.

As shown in FIGS. 1 and 2, micro-channel chip 10 includes lower plate member (substrate member) 12 that is transparent and has a substantially rectangular planar shape and upper plate member (cover member) 14.

The thickness of lower plate member 12 is approximately one millimeter, and the thickness of upper plate member 14 is approximately several tens of micrometers to one millimeter. Further, the external dimensions of lower and upper plate members 12 and 14 are generally the same. The length of the longer side of the plate member is about fifty millimeters, and the length of the shorter side is about twenty millimeters.

Lower and upper plate members 12 and 14 are both made of a resin material, such as polyethylene terephthalate, polycarbonate, polymethylmethacrylate, vinyl chloride, acryl, polypropylene, polyether, or polyethylene. However, lower and upper plate members 12 and 14 may be made of different materials. Further, when the fluorescence or absorbance is measured in an analysis using the micro-channel chip according to the present invention, parts in lower and upper plate members 12 and 14 that serve as paths for measurement light need to be made of a transparent material. However, parts in the lower and upper plate members other than the measuring light paths may be made of a colored (for example, black) material that does not affect photometry by a light blocking property. Meanwhile, since the surfaces of lower and upper plate members 12 and 14 made of a resin material are generally hydrophobic, the lower and upper plate members have a property that it is difficult to form a film on their surfaces. Accordingly, it is preferable to perform preparatory processing for making the surfaces of plate members hydrophilic by a surface treating means using plasma, UV (Ultraviolet), ozone, and so on, which has been known heretofore, prior to the process of forming a $SiO_2$ film (described later).

Lower and upper plate members 12 and 14 are bonded by adhesion using a transparent organic adhesive, by thermocompression bonding, and so on.

Figure 3:
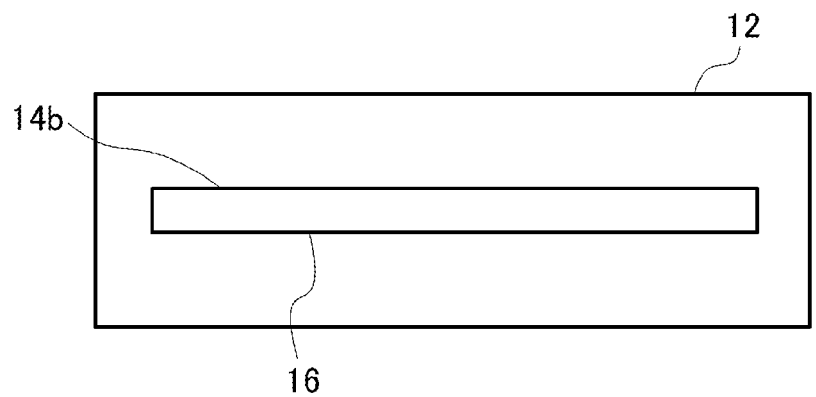
FIG. 3 is a plan view of a lower plate member of the micro-channel chip shown in FIG. 1.
Figure 4:
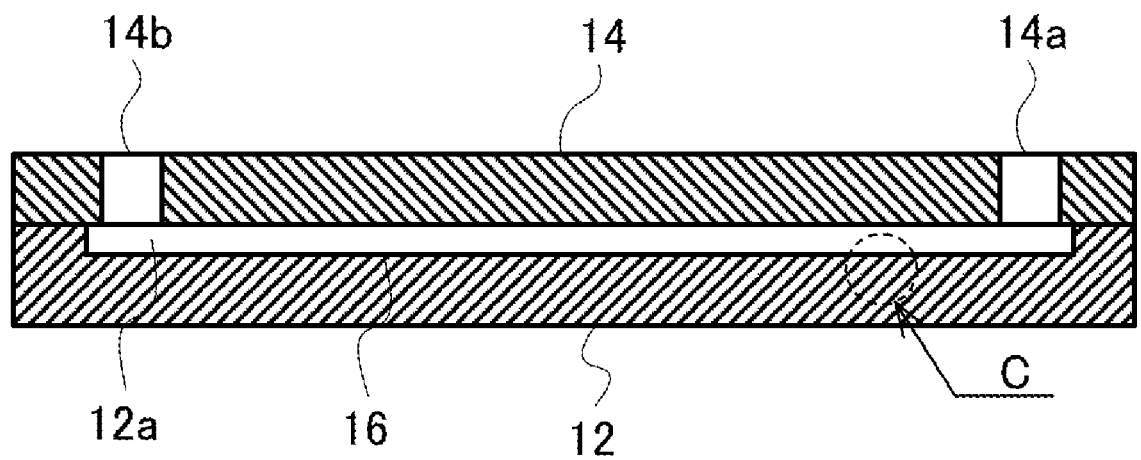
FIG. 4 is a IV-IV cross-sectional view in FIG. 2.
Figure 5:
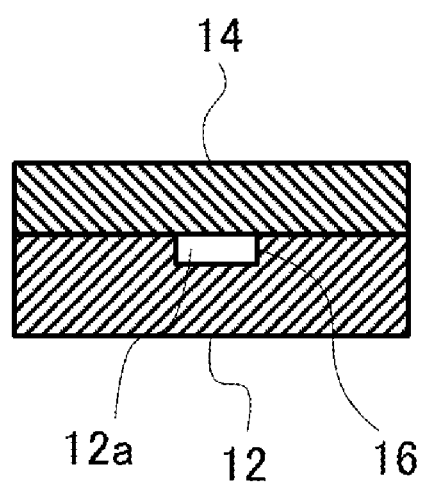
FIG. 5 is a V-V cross-sectional view in FIG. 2.

FIG. 3 is a plan view of the lower plate member, FIG. 4 is a IV-IV cross-sectional view of FIG. 2, and FIG. 5 is a V-V cross-sectional view of FIG. 2.

As shown in FIGS. 3 to 5, linear channel 12a, which extends in the longitudinal direction, is formed in a substantially central part on the surface (upper surface) of lower plate member 12 facing upper plate member 14. Channel 12a has a substantially rectangular cross-section, in which the length of one side is approximately several tens micrometers in width and depth. The channel has a length of about several centimeters.

Through-hole (inlet) 14a having a substantially circular cross-section is formed in upper plate member 14 so as to be open toward one end of channel 12a and the outside. Further, through-hole (outlet) 14b having a substantially circular cross-section is formed in upper plate member 14 so as to be open toward the other end of channel 12a and the outside. Each of through-holes 14a and 14b has a diameter approximately several hundred micrometers to several millimeters, and has a sufficient size to function as an inlet or an outlet for an organic solvent and for the solution to be analyzed.

The inner wall surfaces of through-holes 14a and 14b and channel 12a are entirely coated with $SiO_2$ film 16 in order to prevent ionic hydrophobic substance from adsorbing on the surface of the channel. The feature of the present invention lies in this $SiO_2$ film 16.

[Process of Forming $SiO_2$ Film]

Figure 6B:
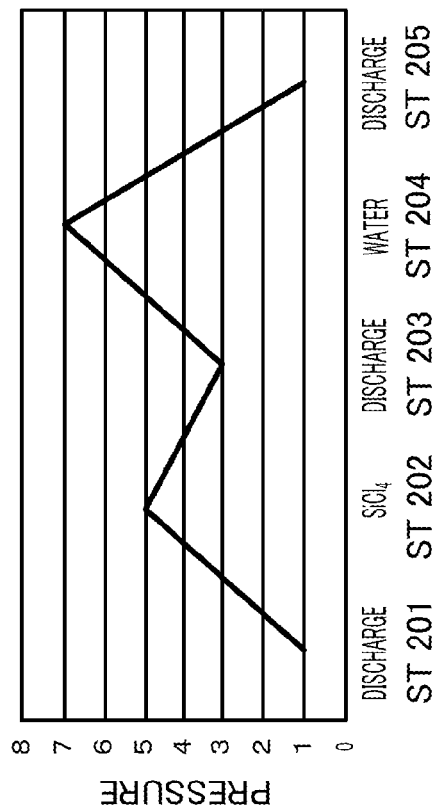
FIG. 6 is a view showing a relationship between pressure and gas used to form a $SiO_2$ film.
Figure 6A:
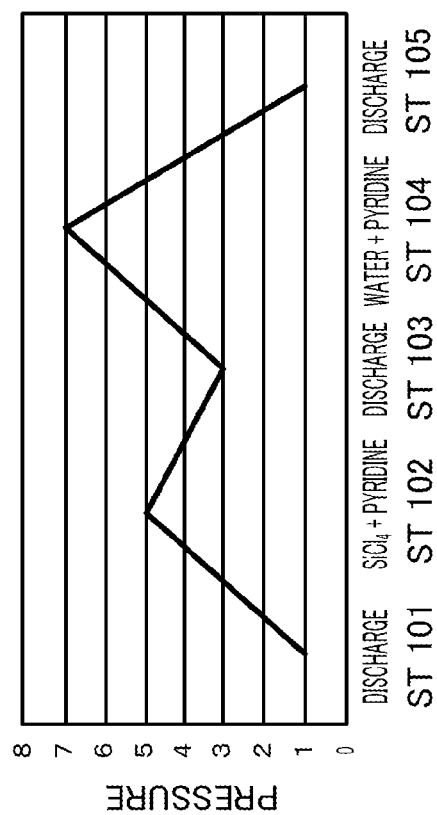

A process of forming the $SiO_2$ film of micro-channel chip 10 according to this embodiment will be described below with reference to FIG. 6. FIG. 6 is a view showing a relationship between pressure (vertical axis) and gas (horizontal axis) used to form the $SiO_2$ film.

First, while micro-channel chip 10 before coating with $SiO_2$ film 16 is set in a chamber in a chemical vapor deposition (CVD) apparatus, air and gas in the chamber are discharged so that the inside of the chamber is vacuumed (ST 101).

Then, silicon tetrachloride ($SiCl_4$) as a silicon precursor gas and pyridine as a catalyst are injected into the chamber (ST 102). Meanwhile, a purge gas and a carrier gas are injected into the chamber along with the precursor gas.

Next, the gases in the chamber are discharged to vacuum the chamber inside (ST 103).

Subsequently, water as an oxidizer for forming $SiO_2$ and pyridine as a catalyst, are injected into the chamber (ST 104). If pyridine is used as a catalyst where water is used as an oxidation source, it is possible to form a film fast, at a high rate, and at a low temperature, as compared with a case where no catalyst is provided.

After that, gas in the chamber is discharged to vacuum the inside of the chamber (ST 105).

Further, ST 101 to ST 105 are repeated until the $SiO_2$ film has a predetermined thickness. Hereinafter, the $SiO_2$ film that is formed through ST 101 to ST 105 and that contacts the resin substrate (lower and upper plate members 12 and 14), will be referred to as the "bottom layer."

The bottom layer uses pyridine, which is an organic component, as a catalyst. Accordingly, the bottom layer contains a high content of carbon atoms.

After the bottom layer is formed, a $SiO_2$ film (hereinafter referred to as the "surface layer"), which exposes on the surface of the channel, is formed through ST 201 to ST 205.

First, the air and gas in the chamber are discharged to vacuum the inside of the chamber (ST 201).

Then, $SiCl_4$ as a silicon precursor gas is injected into the chamber (ST 202). Meanwhile, a purge gas and a carrier gas are injected into the chamber along with the precursor gas.

After that, the gas in the chamber is discharged to vacuum the inside of the chamber (ST 203).

Subsequently, water as an oxidizer used to form $SiO_2$ is injected into the chamber (ST 204).

After that, the gas in the chamber is discharged to vacuum the inside of the chamber (ST 205).

Further, ST 201 to ST 205 are repeated until the $SiO_2$ film (surface layer) has a predetermined thickness.

The surface layer does not use a catalyst (pyridine). Accordingly, the surface layer contains nearly zero content of carbon atoms.

Figure 7:
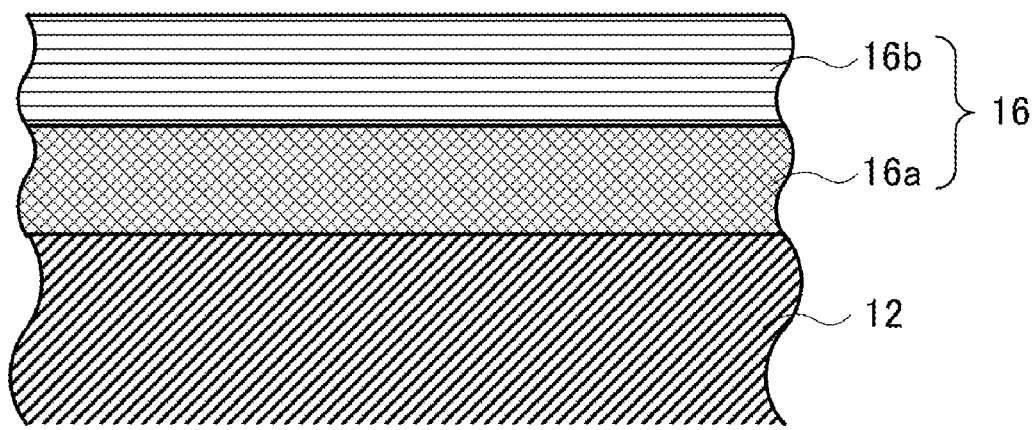
FIG. 7 is an enlarged cross-sectional view of part C in FIG. 4.

In this way, $SiO_2$ film 16 of micro-channel chip 10 formed by the above process has two layers, that is, bottom layer 16*a* that contacts the resin substrates and surface layer 16*b* that exposes on the surface of the channel, as shown in FIG. 7. FIG. 7 is an enlarged cross-sectional view of part C in FIG. 4.

[Electrophoresis by Micro-channel Chip]

If a sample is injected into through-hole (inlet) 14*a* and a voltage is applied to micro-channel chip 10, the sample migrates by electrophoresis in channel 12*a* toward through-hole (outlet) 14*b*. Further, in channel 12*a*, the sample is separated due to the variation in the electrophoresis rate per molecular weight. Accordingly, the tester can find the result of electrophoresis by detecting the fluorescence intensity.

In this case, since the content of carbon atoms is nearly zero in all of the surfaces (surface layer 16*b*) of the inner walls of through-holes 14*a* and 14*b* and channel 12*a*, ionic hydrophobic substance does not adsorb on the surfaces of the inner walls of through-holes 14*a* and 14*b* and channel 12*a*. Accordingly, the tester can find the accurate result of electrophoresis.

[Effects of the Embodiment]

As described above, according to this embodiment, a bottom layer containing a high content of carbon atoms is formed in a part that contacts resin substrates, and a surface layer containing nearly zero carbon atoms is formed in a part that exposes on the surface of a channel. Accordingly, it is possible to coat a micro-channel chip uniformly with a thin $SiO_2$ film, and prevent ionic hydrophobic substance from adsorbing on the surface of the $SiO_2$ film.

Meanwhile, if a catalyst is not used, it may not be possible to deposit a $SiO_2$ film on the resin substrate. Accordingly, it may not be possible to directly form the surface layer, which does not contain carbon atoms, on the resin substrate.

[Modification]

Although a case has been described above with this embodiment where $SiCl_4$ and pyridine are injected in ST 102 in order to form a bottom layer and water and pyridine are injected in ST 104, the present invention is not limited to this, and it is equally possible to use other precursors, oxidation sources, and catalysts.

For example, trimethylaluminum (TMA) may be injected in ST 102 and water may be injected in ST 104. As an example, titanium tetrachloride ($TiCl_4$) may be injected in ST 102 and water may be injected in ST 104. In this case, pyridine as a catalyst is not necessary.

Further, although a case has been described above with this embodiment where a $SiO_2$ film is formed, the present invention is not limited to this, and it is equally possible to use an inorganic oxide film other than a $SiO_2$ film.

Furthermore, although a case has been described above with this embodiment where the content of carbon atoms in the surface layer is nearly zero, the present invention is not limited to this, and it is equally possible to provide a more advantageous effect than the related art if the content of carbon atoms in the surface layer is reduced lower than the bottom layer.

Figure 8:
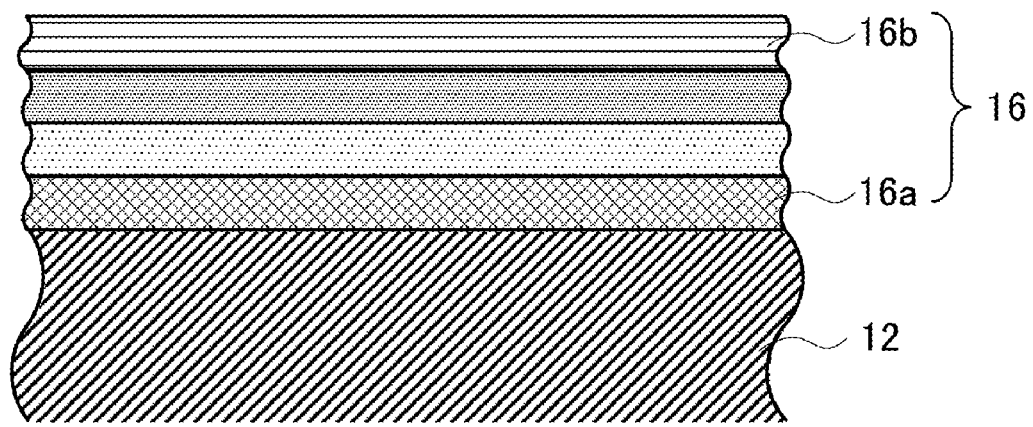
FIG. 8 is an enlarged cross-sectional view of a modification of the micro-channel chip according to an embodiment of the present invention.

Moreover, although a case has been described above with this embodiment where a $SiO_2$ film (inorganic oxide film) with two layers (the bottom layer and the surface layer) is provided, the present invention is not limited to this, and it is equally possible to form a multi-layer $SiO_2$ film with three or more layers, that is, a multi-layer $SiO_2$ film having a bottom layer, a surface layer, and additional layers interposed in between, as shown in FIG. 8. In this case, the content of carbon atoms may be lower nearer the surface layer.

Further, although a case has been described with this embodiment where the inorganic oxide film has multiple layers and the content of carbon atoms in the surface layer is lower than that of the bottom layer, with the present invention, it is equally possible to replace carbon atoms with nitrogen atoms and the content of nitrogen atoms of the surface layer may be lower than that of the bottom layer.

For example, $TiCl_4$ and ammonia may be injected in ST 102, and water and ammonia may be injected in ST 104.

Industrial Applicability

The micro-channel chip and the micro-analysis system according to the present invention may be used in a device for quickly and accurately examining and analyzing a small amount of substance in fields of science and medicine such as such as biochemistry and analytical chemistry.

Reference Signs List

10: Micro-channel chip
12: Lower plate member
12*a*: Channel
14: Upper plate member
14*a*, 14*b*: Through-hole
16: $SiO_2$ film
16*a*: Bottom layer
16*b*: Surface layer

The invention claimed is:

1. A micro-channel chip comprising:
   a resin substrate in which an inner wall surface of a channel is coated with an inorganic oxide film,
   wherein the inorganic oxide film is formed of at least three layers; and
   a content of carbon or nitrogen atoms is lower than a bottom layer, which contacts the resin substrate, nearer to a surface layer that exposes on a surface of the channel.

2. The micro-channel chip according to claim 1, wherein the surface layer is a $SiO_2$ (silicon dioxide) film.

3. The micro-channel chip according to claim 1, wherein the bottom layer is formed using a catalyst of an organic component, and the surface layer is formed without using the catalyst of the organic component.

4. The micro-channel chip according to claim 1, wherein the bottom layer and the surface layer are formed by a CVD method.

5. A micro-analysis system comprising the micro-channel chip according to claim 1.

* * * * *